United States Patent [19]

Schneider et al.

[11] Patent Number: 4,735,969

[45] Date of Patent: Apr. 5, 1988

[54] MENADIONE CHOLINE BISULFITE ADDUCT, ITS PREPARATION AND ANTIHEMORRHAGIC COMPOSITIONS

[75] Inventors: Joachim U. Schneider, Weisenheim; Hans Kiefer, Wachenheim, both of Fed. Rep. of Germany

[73] Assignee: BASF Aktiengesellschaft, Ludwigshafen, Fed. Rep. of Germany

[21] Appl. No.: 799,026

[22] Filed: Nov. 18, 1985

[30] Foreign Application Priority Data

Nov. 28, 1984 [DE] Fed. Rep. of Germany ....... 3443270

[51] Int. Cl.$^4$ .................... C07C 50/14; C07C 143/30; A61K 31/12; A23K 1/16
[52] U.S. Cl. .................... 514/642; 260/396 K; 260/501.19; 514/643; 514/657; 514/681; 514/709; 514/834; 514/973
[58] Field of Search ............ 260/396 K, 501.19; 514/642, 681, 709, 643, 834, 657, 973; 53/507

[56] References Cited

U.S. PATENT DOCUMENTS

| | | | |
|---|---|---|---|
| 2,295,129 | 9/1942 | Riegel et al. | 260/396 K |
| 2,331,808 | 10/1943 | Shelton et al. | 260/396 K |
| 2,827,377 | 3/1958 | Frost | 514/657 |
| 3,328,169 | 6/1967 | Nanninga | 260/396 K |
| 3,947,491 | 3/1976 | Kelly et al. | 260/501.15 |
| 4,577,019 | 3/1986 | Braschi | 260/396 K |

FOREIGN PATENT DOCUMENTS

| | | | |
|---|---|---|---|
| 1033017 | 6/1958 | Fed. Rep. of Germany . | |
| 2855851 | 1/1980 | Fed. Rep. of Germany ... | 260/396 K |
| 996080 | 12/1951 | France | 260/396 K |
| 771180 | 3/1957 | United Kingdom | 260/396 K |
| 2025976 | 1/1980 | United Kingdom | 260/396 K |

OTHER PUBLICATIONS

*The Merck Index,* 8th ed, 1968, p. 254.
M. B. Moore and M. E. Balis, J. Amer. Chem. Soc. 72 (1950) 844–847.
J. C. Vire, G. J. Patriarche and G. D. Christian, Analytical Chemistry 51 (1979) 752 et seq.
J. Nor, J. Kafvi and R. Cohen, Poultry Science, 57 (1978), 206–209 (copy not available).

*Primary Examiner*—Richard L. Raymond
*Assistant Examiner*—Raymond Covington
*Attorney, Agent, or Firm*—John H. Shurtleff

[57] ABSTRACT

A novel bisulfite adduct of menadione, the menadione choline bisulfite adduct, a process for its preparation, and its use as an antihemorrhagic agent.

15 Claims, No Drawings

MENADIONE CHOLINE BISULFITE ADDUCT, ITS PREPARATION AND ANTIHEMORRHAGIC COMPOSITIONS

The present invention relates to a novel bisulfite adduct of menadione, which exhibits vitamin K activity, the preparation of this compound and its use in animal nutrition and as a therapeutic in human and veterinary medicine.

It has long been known that 2-methyl-1,4-naphthoquinone (menadione) has a powerful antihemorrhagic action, and menadione has therefore been considered as being a vitamin of the K series. In the literature, menadione is predominantly referred to as vitamin $K_3$ (cf. Ullmanns Encyklopädie der technischen Chemie, 4th edition, volume 23, page 649 et seq., Verlag Chemie, Weinheim, 1983).

In spite of the excellent antihemorrhagic action of menadione, this product itself has not become commercially important either in human medicine or in animal nutrition. The reasons for this are the insolubility of menadione in water, its low stability to the effects of the environment (heat, light) and its skin-irritating and inflammatory properties.

Products which have an antihemorrhagic action similar to that of menadione but do not possess the disadvantages described above to such a great extent or are free from these disadvantages are the adducts of alkali metal or alkaline earth metal bisulfites with menadione (German Published Application DAS No. 1,033,017, French Pat. No. 996,080, U.S. Pat. No. 2,331,808, British Pat. No. 771,180, etc.). These products, for example the adduct of sodium bisulfite with menadione, which is generally referred to as MSB (menadione sodium bisulfite) in industry, have become very important commercially in the animal feeds industry.

Scientific studies (cf. for example M. Carmack, M. B. Moore and M. E. Balis, J. Amer. Chem. Soc. 72 (1950), 844–847 and J. C. Vire, G. J. Patrlavche and G. D. Christian, Anal. Chem. 51 (1979), 752 et seq.) and experience in the animal feeds industry (J. Nir, J. Kafvi and R. Cohen, Poultry Science, 57 (1978), 206–209) that even MSB, as the most frequently used bisulfite adduct, does not possess sufficient stability to light, heat or moisture.

Attempts have therefore been made to increase the stability of MSB by converting it to more poorly water-soluble products by reaction with suitable salts of weak bases.

Among these compounds, menadione pyrimidinol bisulfite (MPB) is the most widely used compound (cf. U.S. Pat. No. 3,328,169). This adduct contains menadione in an amount of 45.6%, in addition to 32.6% of dimethylpyrimidinol. This compound is in fact more stable, but the higher stability is achieved through the presence of a foreign substance and an intentionally low water-solubility.

According to German Laid-Open Application DOS No. 2,855,851, attempts have therefore been made to replace the stabilizing effect of the foreign substance dimethylpyrimidinol with certain vitamins, such as vitamin $B_1$ or $B_5$ (nicotinic acid or nicotinamide). Although these vitamin adducts are certainly more acceptable from the physiological point of view, they still have the following serious disadvantages:

As in the case of MPB, all the adducts described in German Laid-Open Application DOS No. 2,855,851 possess substantially poorer water-solubility than MSB; all methods of preparation of both MPB and the adducts stated in German Laid-Open Application DOS No. 2,855,851 are based on the fact that the products of the process are substantially less soluble than MSB. In view of the original desire to convert menadione to a readily water-soluble derivative (see above), these products accordingly constitute a backward step.

On the other hand, the compounds stated in German Laid-Open Application DOS No. 2,855,851 possess not only an antihemorrhagic action but also a powerful action corresponding to that of the vitamin used for stabilization (cf. German Laid-Open Application DOS No. 2,855,851, page 8, 3rd paragraph). The two actions are inseparably combined in the claimed compounds. If, for example, the adduct of menadione sulfonic acid with nicotinic acid is to be applied for preventing or curing hemorrhages, nicotinic acid, which has a completely different physiological action, is necessarily added, and vice versa.

It is an object of the present invention to provide a menadione adduct which has a powerful antihemorrhagic action, is readily water-soluble and is substantially more stable than MSB, does not contain any foreign substances and does not possess any additional undesirable extraneous vitamin activity. It is a further object of the present invention to provide a process for the preparation of this adduct.

We have found that this object is achieved by the menadione choline bisulfite adduct of the empirical formula $C_{16}H_{23}O_6NS$ and of the structural formula I

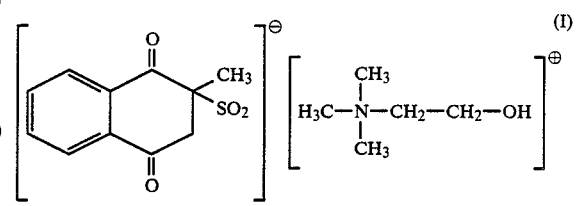

which can be prepared by a method in which menadione is reacted with choline bisulfite in aqueous solution and the product is isolated by crystallization.

The adduct of choline bisulfite with menadione (MCB) has not been described to date in the literature and exhibits an antihemorrhagic action similar to that of MSB and a far greater solubility in water. For example, stable, readily stirrable solutions of MCB in water which contain more than 70% of MCB can be prepared at room temperature, whereas the solubility of MSB is about 40% and that of MPB is only 3%.

Aqueous solutions of MCB show no decrease in vitamin K activity even after storage for several months at room temperature. In comparison, a loss of activity of from 10 to 15% is observed in the case of freshly prepared MSB solutions after storage of only one month at 20° C.

The fact that MCB does not absorb moisture from the air and, unlike most choline salts, does not decompose in the air is surprising.

The novel product is obtained by reacting choline bisulfite with menadione according to the following equation:

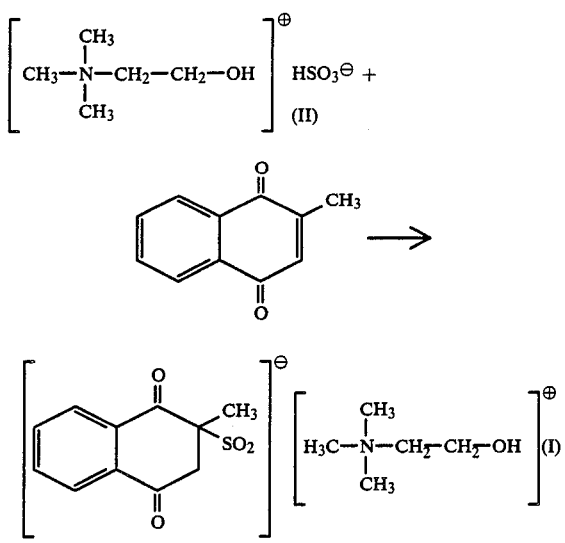

The choline bisulfite of the formula (II) is advantageously prepared in situ by reacting, for example, a commercial, concentrated aqueous choline bicarbonate solution with liquid or gaseous sulfur dioxide until the pH has fallen to 4–5. In general, the choline bicarbonate solution is used in a concentration of from 70 to 80% and in an amount of from 1.0 to 1.1 moles per mole of menadione.

The choline bisulfite is reacted with finely powdered menadione at from 0° to 80° C., preferably from 40° to 50° C. Preferably equimolar amounts of the two components are chosen, or from 1 to 1.1 moles of choline bisulfite per mole of menadione.

The course of the reaction can be monitored directly since as the menadione is insoluble in water whereas the product MCB is readily water-soluble. When all of the menadione has gone into solution in the form of the menadione choline bisulfite adduct (MCB), which as a rule takes from 3 to 5 hours, the MCB is preferably isolated from the reaction mixture in the following manner: a solvent which is miscible with water, and reduces the solubility of the MCB in water, and in which the MCB is insoluble or sparingly soluble, is added at room temperature, so that the MCB crystallizes out.

Examples of suitable solvents which result in the MCB crystallizing readily and substantially are alcohols of 3 carbon atoms and water-miscible ethers, eg. tetrahydrofuran or dioxane. Isopropanol is particularly useful and is generally added in an amount of from 50 to 500, in particular from 200 to 300, % by weight, based on the crude reaction mixture. To complete the crystallization, the reaction mixture is cooled, for example to 0° C.

The crystals which have separated out are then isolated from the solution in a conventional manner, for example by filtration, and are dried.

The menadione choline bisulfite adduct obtained in high yield and purity by the novel process is free of water of crystallization, possesses excellent solubility in water and gives aqueous solutions having a pH of 4.5–5.5. The percentage of menadione can be determined by the method described in US Pharmacopeia, 15th edition, page 394; this method shows that the menadione content is from 47 to 48% (theory: 48.2%). For use in pharmaceutical formulations, MCB can be further purified by recrystallization from anhydrous lower alcohols.

Because of its good properties, such as high purity, excellent water solubility and high stability, which are achieved with the physiologically completely acceptable building block choline, MCB is very useful as an antihemorrhagic agent in human and veterinary medicine.

The solubility of MCB is so high that isotonic solutions can be prepared without the addition of sodium chloride.

Examples of pharmaceutical formulations which contain MCB as the essential active compound are elixirs, ointments, capsules, tablets and sterile isotonic aqueous solutions. The dose is in general of the same order of magnitude as is usually employed for conventional menadione compounds.

MCB is also very useful in animal nutrition, for example as a vitamin additive in animal feeds or drinking liquids, for the prophylactic treatment of hemorrhages.

To improve the pourability or the flow behavior, conventional anticaking agents, eg. special silicas, phosphates or calcium salts of fatty acids, can be added to solid MCB.

The amount of MCB is in general from 0.1 to 5 mg per kg of feed. Advantageously, an appropriate vitamin premix consisting of vitamins and carrier and adapted to the requirements of the particular animal species is first prepared. This active compound concentrate contains MCB in an amount of from 5 to 50, in particular from 10 to 30, g per kg of concentrate, and is mixed with other feed components to give a premix, from which the actual feed is prepared by mixing with further components. A typical vitamin premix is given in Example 3.

Drinking liquids generally contain MCB in an amount of from 1 to 5 mg per liter. Formulations for drinking liquids contain MCB in amounts of 0.5–2.5%.

EXAMPLE 1

Gaseous sulfur dioxide is passed, while stirring constantly, into 363 g of a 75% strength aqueous choline bicarbonate solution until the pH reaches 4.5. 258 g of finely powdered menadione are then introduced at from 40° to 45° C., with continued stirring. The menadione goes completely into solution in the course of 4 hours. 1500 ml of isopropanol are added, after which the mixture is cooled to 0° C. in the course of 3 hours, and the crystals which separate out are filtered off over a frit, washed with 300 ml of isopropanol, and dried on the frit by blowing through dry air or dry nitrogen. 465 g of virtually colorless crystals of melting point 128° C. and having a menadione content (according to US Pharmacopeia) of 47.5% (theory: 48.2%) are obtained. Yield: 85.6% of theory (ratio of amount of menadione found analytically to the amount of menadione used).

$C_{16}H_{23}O_6$ NS (molecular weight 357): calcualted: C 53.8%, H 6.4%. O 26.9%, N 3.9%, S 8.9%; found: c 53.5%, H 6.4%, O 26.6%. N 4.0%, S 8.9%

The NMR spectrum completely confirms the structure shown above.

EXAMPLE 2

20% strength solutions of commercial MSB and of MCB obtainable as described in Example 1, in $D_2O$, are heated at 80° C. for 6 hours. The NMR spectra of the two solutions are recorded before and after heating. It is found that, in the case of the heated sample of MCB, no new NMR signals appear and the existing lines do not show any change in intensity.

NMR analysis shows that, under the same conditions, 36% of the MSB is converted to the isomeric compound which does not possess any vitamin K activity (cf. J. Amer. Chem. Soc. 65 (1943), 1210).

| EXAMPLE 3 | |
|---|---|
| Vitamin premix | |
| Vitamin A 500,000 IU/g | 144.7 kg |
| Vitamin D$_3$ 500,000 IU/g | 18.1 kg |
| Vitamin E 50% | 160.8 kg |
| Vitamin B$_1$ | 9.3 kg |
| Vitamin B$_2$ | 74.5 kg |
| Vitamin B$_6$ | 12.4 kg |
| Vitamin B$_{12}$ (2%) | 2.0 kg |
| Vitamin C | 120.6 kg |
| Vitamin K$_3$ in the form of MCB | 12.1 kg |
| Folic acid | 3.0 kg |
| Nicotinic acid | 120.6 kg |
| Ca D-pantothenate | 63.4 kg |
| Soybean oil | 10.0 kg |
| Wheat bran (carrier) | 248.5 kg |
| | 1,000.0 kg |

We claim:

1. The crystalline menadione choline bisulfite adduct of the formula

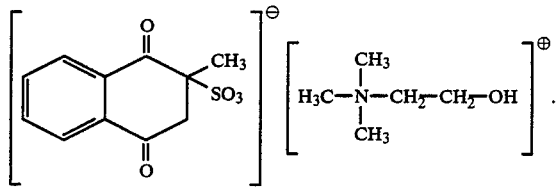

2. A process for the preparation of the menadione choline bisulfite adduct of the formula

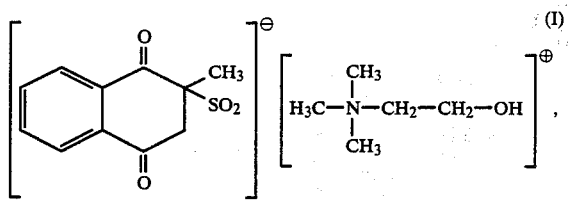

which comprises:
reacting menadione with choline bisulfite in aqueous solution at 0°–80° C. until the pH has fallen to about 4–5; and
isolating the product (I) by crystallization.

3. A process as claimed in claim 2, wherein the choline bisulfite is prepared in situ from concentrated, aqueous choline bicarbonate solution and sulfur dioxide.

4. A process as claimed in claim 2, wherein a water-miscible solvent which reduces the solubility of the menadione choline bisulfite adduct in water and in which the adduct is insoluble or sparingly soluble is added when the reaction is complete.

5. A process as claimed in claim 4, wherein, when the reaction is complete, isopropanol is added in an amount of from 50 to 500% by weight, based on the crude reaction mixture.

6. The adduct as claimed in claim 1 in a water soluble crystalline form substantially free of water.

7. The adduct as claimed in claim 6, which has been purified by recrystallization from anhydrous lower alcohols.

8. A pharmaceutical composition comprising an effective antihemorrhagic amount of the menadione choline bisulfite adduct of the formula

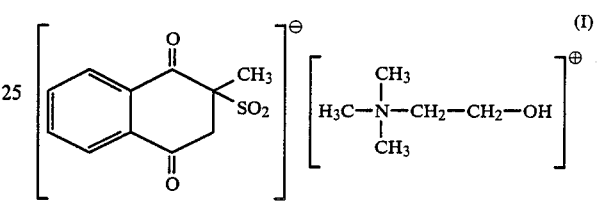

and a carrier therefor.

9. A composition as claimed in claim 8 wherein the carrier is a sterile isotonic aqueous solution.

10. A composition as claimed in claim 8 wherein the adduct (I) is in crystalline form admixed with a carrier which is also in solid form.

11. A composition as claimed in claim 8 in which the carrier includes an animal feed in solid to liquid form containing a small amount of the adduct (I) sufficient to provide a prophylactic treatment of hemorrhages.

12. A composition as claimed in claim 11 which is an animal feed in solid form containing from 0.1 to 5 mg of the adduct (I) per kg of feed.

13. A composition as claimed in claim 11 which is a drinking liquid for animals containing from 1 to 5 mg of the adduct (I) per liter of liquid.

14. A composition as claimed in claim 11 in the form of a concentrate containing at least one vitamin additive and the adduct (I) in an amount of from 5 to 50 g per kg of concentrate.

15. A composition as claimed in claim 14 wherein the adduct (I) is present in an amount of 10 to 30 g per kg of concentrate.

* * * * *

UNITED STATES PATENT AND TRADEMARK OFFICE
CERTIFICATE OF CORRECTION

PATENT NO. : 4,735,969
DATED : April 5, 1988
INVENTOR(S): SCHNEIDER et al

It is certified that error appears in the above-identified patent and that said Letters Patent is hereby corrected as shown below:

IN THE SPECIFICATION

Columns 2 and 3; and

IN THE CLAIMS

Claims 2 and 8:

The substituent "$SO_2$" which appears in the left-hand bracket of the structural formula should be corrected to read --$SO_3$--.

Signed and Sealed this

Second Day of August, 1988

Attest:

DONALD J. QUIGG

Attesting Officer     Commissioner of Patents and Trademarks